United States Patent
Miyachi

(10) Patent No.: US 9,949,707 B2
(45) Date of Patent: Apr. 24, 2018

(54) RADIOGRAPHIC IMAGING SYSTEM, CONTROL METHOD, AND STORAGE MEDIUM

(71) Applicant: CANON KABUSHIKI KAISHA, Tokyo (JP)

(72) Inventor: Norihiko Miyachi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 228 days.

(21) Appl. No.: 15/082,955

(22) Filed: Mar. 28, 2016

(65) Prior Publication Data

US 2016/0287202 A1 Oct. 6, 2016

(30) Foreign Application Priority Data

Mar. 31, 2015 (JP) .................................. 2015-072863

(51) Int. Cl.
*G01D 18/00* (2006.01)
*A61B 6/00* (2006.01)

(52) U.S. Cl.
CPC .......... *A61B 6/5241* (2013.01); *A61B 6/4266* (2013.01); *A61B 6/461* (2013.01)

(58) Field of Classification Search
CPC ....... A61B 6/4233; A61B 6/542; A61B 6/463; A61B 6/4405
See application file for complete search history.

(56) References Cited

U.S. PATENT DOCUMENTS 9,423,517 B2 * 8/2016 Kang ...................... G01T 7/005

FOREIGN PATENT DOCUMENTS

JP 2012-045159 A 3/2012

* cited by examiner

*Primary Examiner* — Don Wong
(74) *Attorney, Agent, or Firm* — Canon USA Inc., IP Division

(57) ABSTRACT

A radiographic imaging system, which includes a plurality of radiographic imaging apparatuses each configured to acquire a radiographic image and a processing unit configured to combine a plurality of the radiographic images acquired from the plurality of radiographic imaging apparatuses to generate a stitched image, includes a correction image data determination unit configured to determine correction image data based on an irradiation condition of radiation to be emitted from the radiation source, and an image correction unit configured to correct an area of the stitched image corresponding to an area in which the plurality of radiographic imaging apparatuses overlap, by using the correction image data.

16 Claims, 12 Drawing Sheets

FIG.4

| | | CONDITION (3): DEPTH 1 | | | | CONDITION (3): DEPTH 1 | | | |
|---|---|---|---|---|---|---|---|---|---|
| | | CONDITION (1): HEIGHT 1 | ~ | CONDITION (1): HEIGHT N | CONDITION (1): HEIGHT 1 | ~ | CONDITION (1): HEIGHT N | CONDITION (1): HEIGHT 1 |
| CONDITION (4): TUBE VOLTAGE 1 | CONDITION (2): DISTANCE 1 | CORRECTION DATA 1 | | | | | | |
| | CONDITION (2): DISTANCE M | | | | | | | |
| ~ | CONDITION (2): DISTANCE 1 | | | | | | | |
| | CONDITION (2): DISTANCE M | | | | | | | |
| CONDITION (4): TUBE VOLTAGE J | CONDITION (2): DISTANCE 1 | | | | | | | |
| | CONDITION (2): DISTANCE M | | | | | | | CORRECTION DATA N×I×M×J |

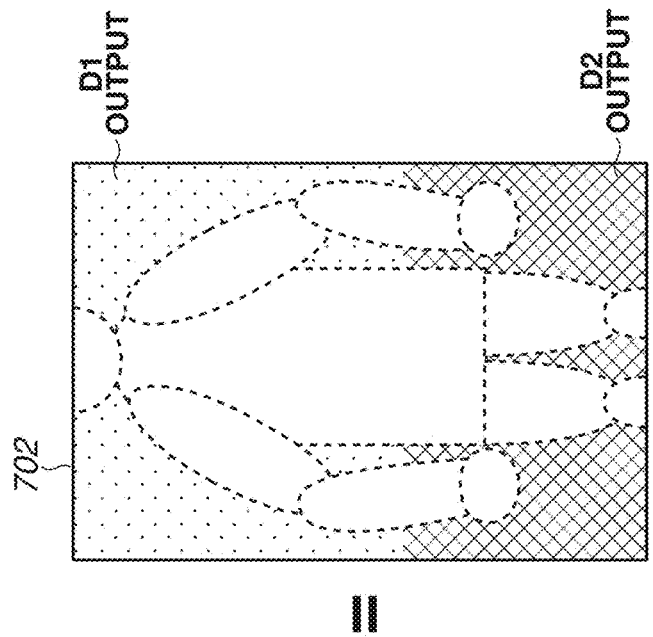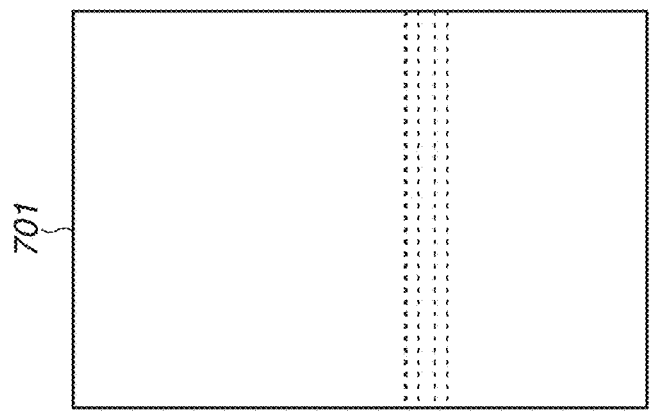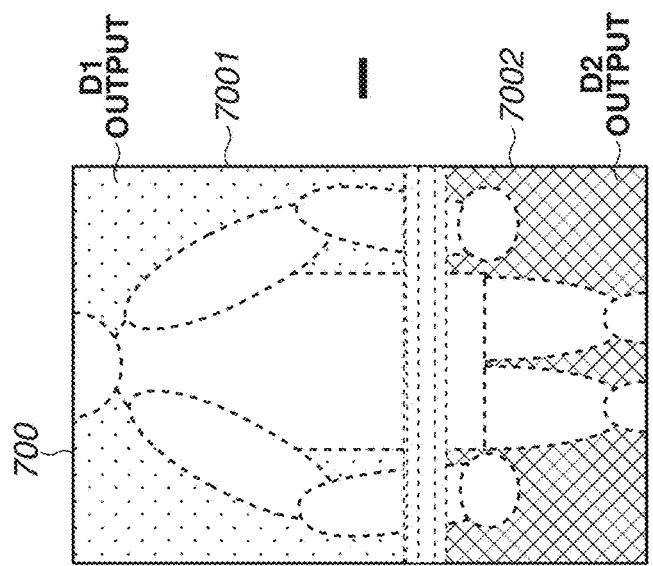

FIG.8

| | | HEIGHT 100 cm | HEIGHT 105 cm | HEIGHT 110 cm | HEIGHT 115 cm | HEIGHT 120 cm | HEIGHT 125 cm | HEIGHT 130 cm | ~ | HEIGHT N |
|---|---|---|---|---|---|---|---|---|---|---|
| DEPTH I | | | | | | | | | | |
| TUBE VOLTAGE J | DISTANCE 150 cm | A | B | C | D | E | F | G | | |
| | DISTANCE 155 cm | H | I | J | K | L | M | N | | |
| | DISTANCE 160 cm | O | P | Q | R | S | T | U | | |
| | DISTANCE 165 cm | V | W | X | Y | Z | a | b | | |
| | DISTANCE 170 cm | c | d | e | f | g | h | i | | |
| | DISTANCE 175 cm | j | k | l | m | n | o | p | | |
| | DISTANCE 180 cm | q | r | s | t | u | v | w | | |
| | ~ | | | | | | | | | |
| | DISTANCE M | | | | | | | | | CORRECTION DATA N×I×M×J |

FIG.9

| | | | | | DEPTH I | | | | | | |
|---|---|---|---|---|---|---|---|---|---|---|---|
| | HEIGHT 100 cm | HEIGHT 105 cm | HEIGHT 110 cm | HEIGHT 115 cm | HEIGHT 120 cm | HEIGHT 125 cm | HEIGHT 130 cm | ~ | HEIGHT N | |
| DISTANCE 150 cm | A | B | C | D | E | F | G | | | |
| DISTANCE 155 cm | H | I | J | K | L | M | N | | | |
| DISTANCE 160 cm | O | P | Q | R | S | T | U | | | |
| DISTANCE 165 cm | V | W | X | Y | Z | a | b | | | |
| DISTANCE 170 cm | c | d | e | f | g | h | i | | | |
| DISTANCE 175 cm | j | k | l | m | n | o | p | | | |
| DISTANCE 180 cm | q | r | s | t | u | v | w | | | |
| ~ | | | | | | | | | | |
| DISTANCE M | | | | | | | | | CORRECTION DATA N×I×M×J | |
| | | | | TUBE VOLTAGE J | | | | | | |

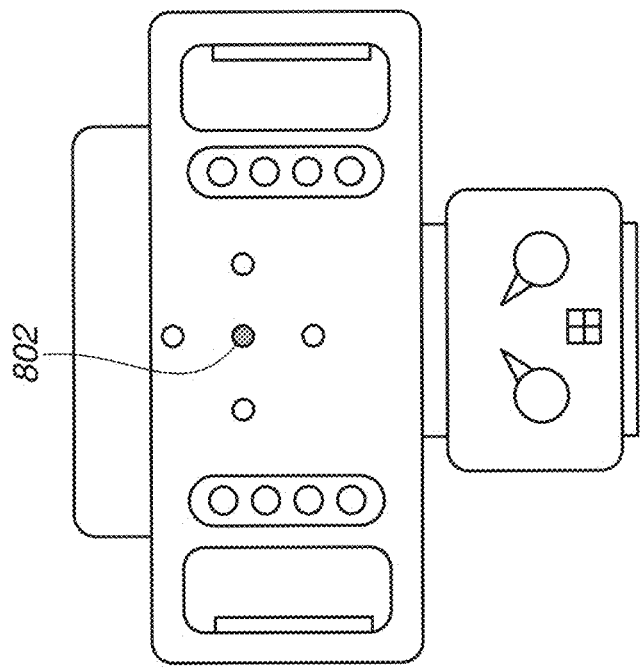
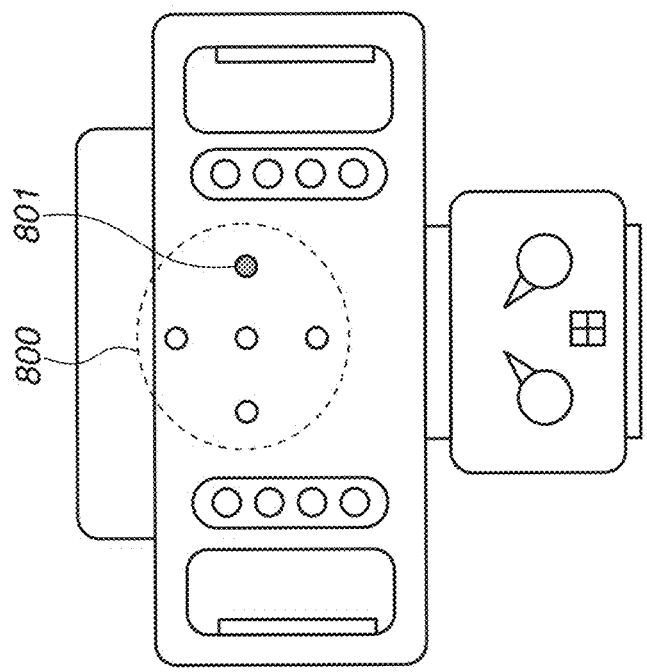

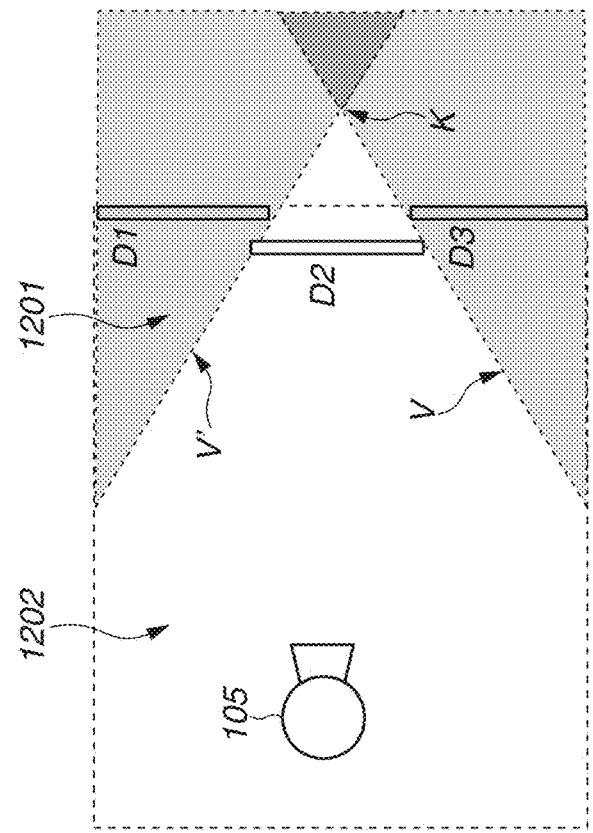
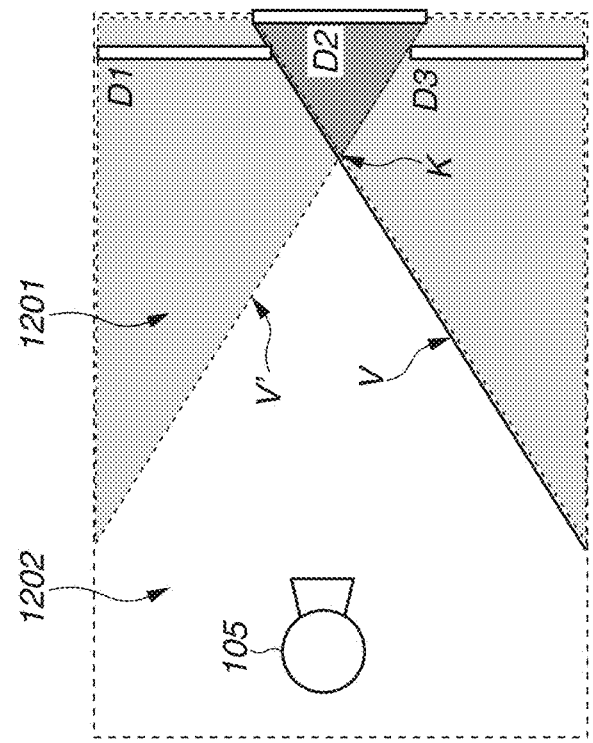
FIG.12A
FIG.12B ent invention.

RADIOGRAPHIC IMAGING SYSTEM, CONTROL METHOD, AND STORAGE MEDIUM

BACKGROUND OF THE INVENTION

Field of the Invention

The present invention relates to a radiographic imaging system using a plurality of radiographic imaging apparatuses, a control method, and a storage medium.

Description of the Related Art

There has recently been a demand for imaging of a long observation area (hereinafter, referred to as long-length imaging or stitch imaging). Examples of stitch imaging in the medical field include imaging of the spinal cord, the entire lower limbs, and the whole body of a subject for examination or diagnostic purposes.

Japanese Patent Application Laid-Open No. 2012-045159 discusses a radiographic imaging system in which a plurality of radiographic imaging apparatuses is arranged to perform stitch imaging.

The radiographic imaging system discussed in Japanese Patent Application Laid-Open No. 2012-045159 captures an image in a state that portions of the plurality of radiographic imaging apparatuses overlap with each other. As a result, an image (radiographic image) captured by a radiographic imaging apparatus that is positioned far from a radiation source may include a structure (image artifact) of a radiographic imaging apparatus that is positioned near the radiation source. An image artifact is any feature which appears in an image which is not present in the original imaged object. In the case of radiographic stitched image, the structure of overlapping of imaging apparatuses (detectors) tends to generate an image artifact. A density and a position in which the structure (artifact) appears in the captured radiographic image change depending on imaging conditions such as a distance between the radiographic imaging apparatuses and a positional relationship between the radiation source and each of the radiographic imaging apparatuses.

The present invention is directed to a radiographic imaging system generating a stitched image by combining a plurality of radiographic images obtained using a plurality of radiographic imaging apparatuses. Such a radiographic imaging system is capable of reducing an adverse effect of a structure appearing in the stitched image, regardless of the imaging conditions.

SUMMARY OF THE INVENTION

According to an aspect of the present invention, a radiographic imaging system, which includes a plurality of radiographic imaging apparatuses each configured to acquire a radiographic image and a processing unit configured to combine a plurality of the radiographic images acquired from the plurality of radiographic imaging apparatuses to generate a stitched image, includes a correction image data determination unit configured to determine correction image data based on an irradiation condition of the radiographic image, and an image correction unit configured to correct an area of the stitched image corresponding to an area in which the plurality of radiographic imaging apparatuses overlap, by using the correction image data.

Further features of the present invention will become apparent from the following description of exemplary embodiments with reference to the attached drawings.

BRIEF DESCRIPTION OF THE DRAWINGS

FIG. 4 is a correction data table according to the first exemplary embodiment.

FIGS. 7A, 7B, and 7C are diagrams illustrating correction processing according to the first exemplary embodiment.

FIG. 8 is a table illustrating correction image data according to the first exemplary embodiment.

FIG. 9 is a table illustrating correction image data according to a second exemplary embodiment of the present invention.

FIGS. 10A and 10B are diagrams illustrating a radiation source according to a third exemplary embodiment of the present invention.

FIGS. 12A and 12B are diagrams illustrating arrangement of a plurality of radiographic imaging apparatuses according to a sixth exemplary embodiment of the present invention.

DESCRIPTION OF THE EMBODIMENTS

Figure 1:
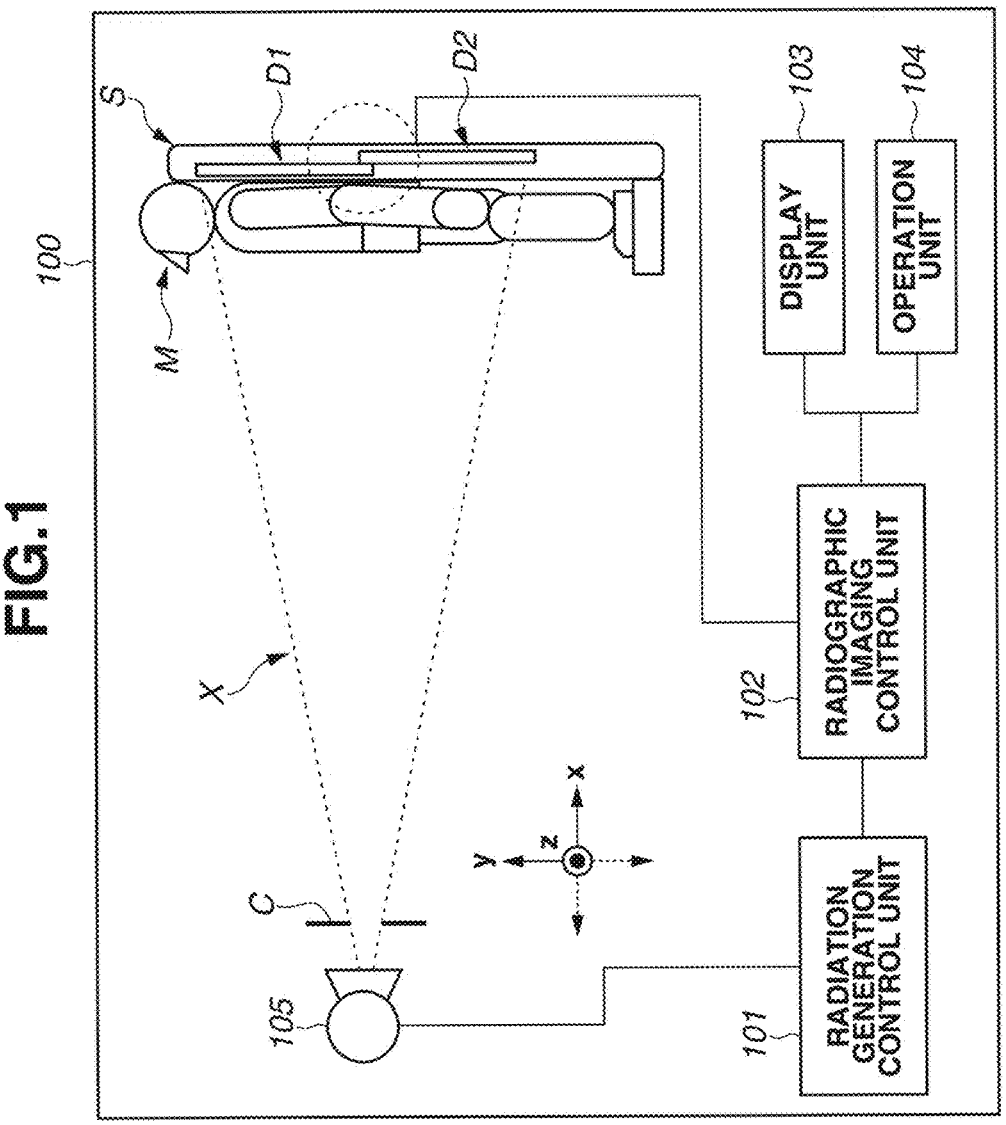
FIG. 1 is a diagram illustrating a radiographic imaging system according to a first exemplary embodiment of the present invention.

Various exemplary embodiments, features, and aspects of the present invention will be described in detail below with reference to the accompanying drawings. However, sizes and configurations described in each of the exemplary embodiments are not limited to those described in this patent specification or illustrated in the drawings. In this specification, radiation includes not only an X ray, but also an alpha ray, a beta ray, a gamma ray, a corpuscular ray, and a cosmic ray.

A first exemplary embodiment of the present invention is described below. First, a radiographic imaging system 100 is described with reference to FIG. 1. The radiographic imaging system 100 performs an examination (captures an image) based on an examination order including a plurality of pieces of examination information. The examination information includes imaging protocol information. Each of imaging protocols defines an image capturing condition and contents of image processing that is performed on a captured image. More specifically, the imaging protocol includes parameter information or imaging execution information, and imaging environment information. The parameter information or the imaging execution information is used at the time of imaging or image processing, and the imaging environment information indicates, for example, a sensor type and an imaging orientation. Moreover, the examination information includes information for identifying an examination order or information for identifying a captured image according to an examination order. The information for identifying an examination order includes an examination identification (ID) and a receipt number.

The radiographic imaging system 100 includes at least a radiographic imaging control unit 102 and a plurality of radiographic imaging apparatuses D1 and D2. The radiographic imaging system 100 further includes a radiation generation control unit 101, a display unit 103, an operation unit 104, and an imaging table S. Although the radiographic imaging system 100 includes two radiographic imaging apparatuses (D1 and D2), a configuration thereof is not limited thereto. The radiographic imaging system 100 may include three or more radiographic imaging apparatuses. The radiographic imaging system 100 combines images (radiographic images) acquired by each of the radiographic imaging apparatuses D1 and D2 to acquire a stitched image. One example of the stitched image is an image acquired by combining radiographic images that are captured when a plurality of radiographic imaging apparatuses is simultaneously irradiated with radiation. Moreover, the stitched image can be an image acquired by combining radiographic images that are acquired when a plurality of radiographic imaging apparatuses is sequentially irradiated with radiation with a predetermined time difference. Herein, the radiographic image is an image that is obtained by acquiring image data by the radiographic imaging apparatus detecting radiation.

In the present exemplary embodiment, a part of a structure of the radiographic imaging apparatus D1 appears in a radiographic image acquired by the radiographic imaging apparatus D2. In a stitched image, as described below, a region in which a plurality of radiographic imaging apparatuses overlaps can be corrected using correction image data to reduce influence (to remove an artifact) of the structure appearing the stitched image. To that end, the correction image data can be determined based on imaging conditions of a radiographic image. Herein, the imaging conditions include at least position information about positions of the plurality of radiographic imaging apparatuses D1 and D2 and a radiation source 105. An example of the radiation source 105 includes an X-ray source, and an example of radiographic imaging apparatuses D1 and D2 includes an X-ray sensor, such as a flat panel detector (FPD). Accordingly, an example of the radiographic image acquired by the radiographic imaging apparatus is an X-ray image. The position information includes an incident angle between each of the plurality of radiographic imaging apparatuses D1 and D2 and radiation emitted from the radiation source 105, and a positional relationship between the radiographic imaging apparatuses D1 and D2. In addition, the position information includes at least a distance X, a height Y, and a depth Z. In FIG. 1, symbols X, Y, and Z respectively represent coordinates of the distance X, the height Y, and the depth Z. The imaging conditions may further include a value relating to a tube voltage of the radiation source 105. In other words, the imaging conditions represent various conditions that may affect image quality, such as a structure that appears when a radiographic image is acquired. Hereinafter, each part or unit of the radiographic imaging system 100 is described.

The radiation source 105 has a function of emitting radiation to the plurality of radiographic imaging apparatuses D1 and D2. In the exemplary embodiment, the radiation source 105 includes an X-ray tube, and irradiates a subject (i.e., an examinee) M with radiation (herein, an X-ray). A collimator C that restricts a radiation irradiation area is arranged between the radiation source 105 and the examinee M. The radiation source 105 irradiates the radiographic imaging apparatuses D1 and D2 with radiation under the imaging conditions such as a predetermined angle, a tube voltage, and a positional relationship (distance X, height Y, and depth Z). Such imaging conditions can be changed as appropriate according to a size of an examinee and the imaging conditions.

The radiation generation control unit 101 controls generation of radiation based on control performed by the radiographic imaging control unit 102. In particular, the radiation generation control unit 101 applies voltage to the radiation source 105 according to an imaging condition corresponding to an imaging protocol, so that the radiation source 105 generates radiation. Moreover, the radiation generation control unit 101 can control the collimator C for adjusting a radiation field and intensity of the radiation. The radiation generation control unit 101 has a function of recognizing position information of the radiation source 105.

Each of the radiographic imaging apparatuses D1 and D2 acquires a radiographic image based on radiation that has transmitted through the examinee M. Moreover, the radiographic imaging apparatuses D1 and D2 may be integrated with the imaging table S. Alternatively, the radiographic imaging apparatuses D1 and D2 of portable type can be independently attached to the imaging table S.

The imaging table S defines arrangement of the radiographic imaging apparatuses D1 and D2. One example of such arrangement is that the radiographic imaging apparatus D1 is arranged on an upper side of a position directly facing the radiation source 105. Meanwhile, the radiographic imaging apparatus D2 is arranged on a lower side of the radiographic imaging apparatus D1 and on a back side of the radiographic imaging apparatus D1. The examinee M stands on a step stool placed in front of the imaging table S, so that a position of the examinee M is defined with respect to the imaging table S and the radiation source 105.

The radiographic imaging control unit 102 comprehensively controls radiographic processing based on the imaging conditions. The radiographic imaging control unit 102 functions as a transmission unit for transmitting various information to the radiation generation control unit 101, and as a reception unit for receiving various information from the radiation generation control unit 101. The radiographic imaging control unit 102 performs image processing on captured images acquired from the radiographic imaging apparatuses D1 and D2. The image processing includes combining processing in which the plurality of captured images from the respective radiographic imaging apparatuses D1 and D2 is combined, correction processing, gradation processing, and frequency processing. The radiographic imaging control unit 102 displays the acquired captured images and a stitched image generated by combining these captured images on the display unit 103. Moreover, the radiographic imaging control unit 102 can transmit the acquired captured images and the stitched image acquired by combining these captured images to a picture archiving and communication system (PACS) or an external device such as a printer.

The display unit 103 displays a stitched image and information such as a state of the radiographic imaging system 100 to an operator. In other words, the display unit 103 has a function of displaying a stitched image and a state of each of the radiographic imaging apparatuses D1 and D2. Moreover, the display unit 103 may display a state of only one of the plurality of radiographic imaging apparatuses. The display unit 103 may be, for example, a display. For example, the display unit 103 can display an examination order received from a radiology information system (RIS) or an examination order made by the operator of the radiographic imaging system 100, and correction image data, which will be described below.

The operation unit 104 acquires an instruction from the operator. The operation unit 104 includes, for example, various buttons or a graphical user interface (GUI) such as a keyboard, a mouse, and a touch panel. For example, the operator can input an image replication instruction to the radiographic imaging system 100 via the operation unit 104.

Figure 2A:
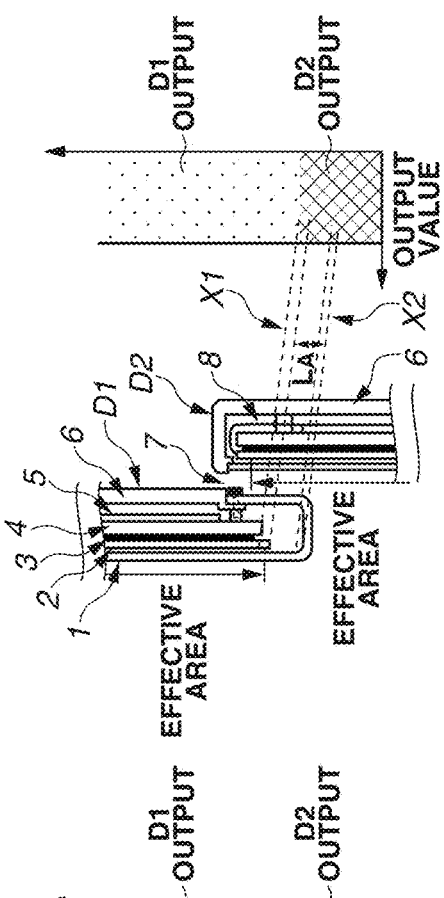
FIGS. 2A, 2B, 2C, and 2D are diagrams each illustrating a relationship between a plurality of radiographic imaging apparatuses and an irradiation angle according to the first exemplary embodiment.

An area in which the radiographic imaging apparatuses D1 and D2 overlap is described with reference to FIGS. 2A, 2B, 2C, and 2D. As illustrated in FIG. 2A, each of the radiographic imaging apparatuses D1 and D2 includes a radiation detection panel 2, an integrated circuit mounted on a flexible circuit substrate 8 and/or a printed circuit board 5, and a casing 6 that houses these components. The radiation detection panel 2 can include a direct conversion sensor for directly converting radiation such as a-Se into electric signals, and an indirect sensor using a photoelectric conversion element and a scintillator such as CsI. The radiation detection panel 2 includes a pixel array including a plurality of pixels arranged in a two-dimensional matrix, and converts emitted radiation into image signals. The integrated circuit or a control circuit (not illustrated) converts the image signals into digital data, so that a radiographic image is acquired. The integrated circuit mounted on the flexible circuit substrate 8 or the printed circuit board 5 is electrically connected to the radiation detection panel 2.

The casing 6 of one of the plurality of radiographic imaging apparatuses spatially overlaps the other casing 6 of the other radiographic imaging apparatus. In the present exemplary embodiment, an effective pixel area (an effective area) of the radiographic imaging apparatus D2 is arranged so as to overlap a portion of the casing 6 of the radiographic imaging apparatus D1 via a gap. Such an arrangement causes reduction of a signal acquired from pixels spatially overlapping the radiographic imaging apparatus D1 in image signals acquired by the radiographic imaging apparatus D2. In other words, in a stitched image acquired after radiographic images are combined, an artifact (a false image or a defect portion) can occur in an area in which the plurality of radiographic imaging apparatuses overlaps. The phrase "to spatially overlap" used herein can include a case where the radiographic imaging apparatuses overlap by being brought into direct or indirect physical contact with each other, and a case where the radiographic imaging apparatuses overlap via a space without physically contacting each other.

Figure 2B:
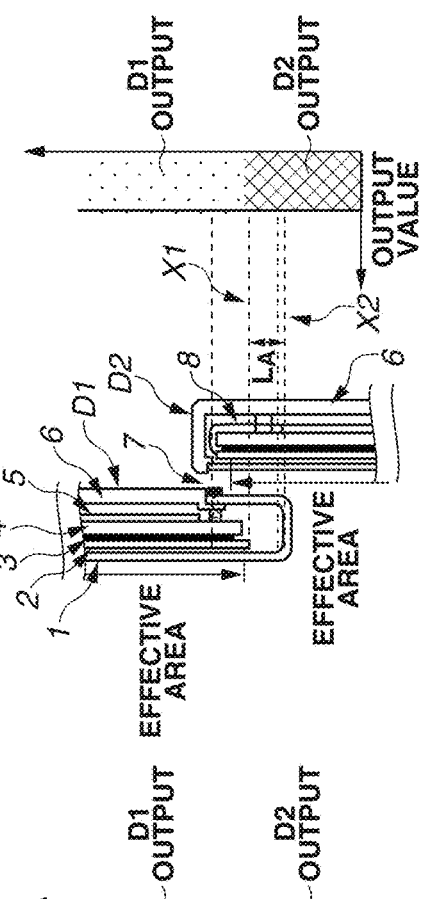
Figure 2C:
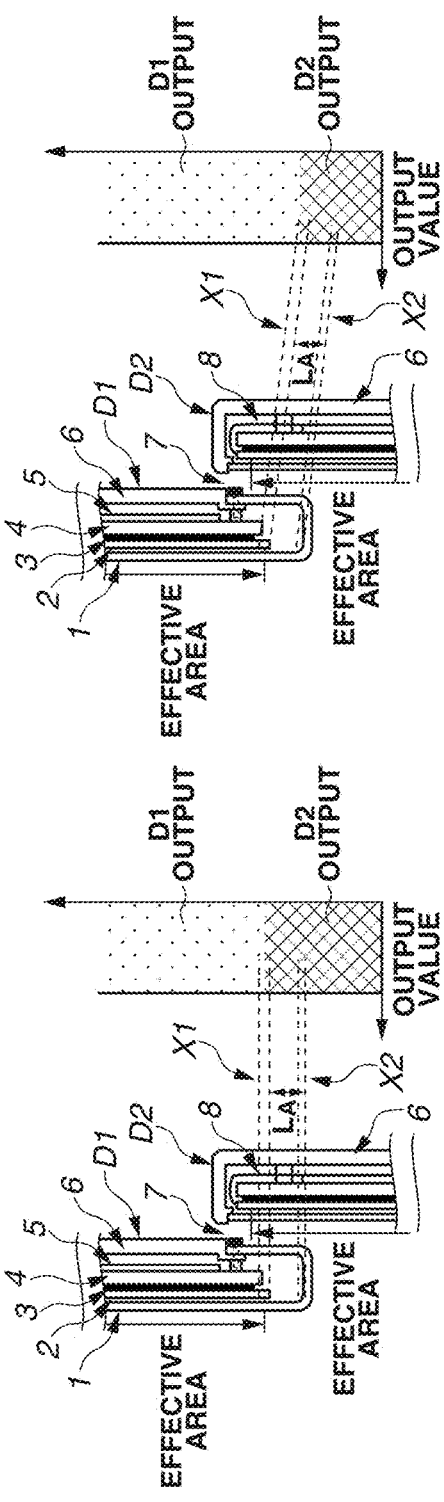
Figure 2D:
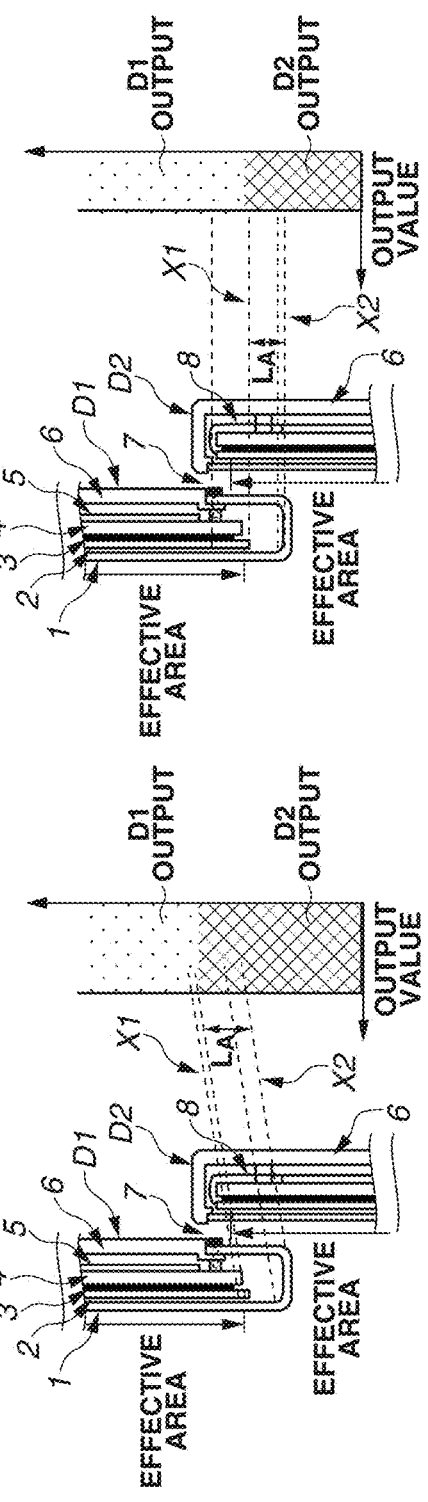

A relationship between an overlapping portion of the radiographic imaging apparatuses D1 and D2 and an incident angle of radiation is described with reference to FIGS. 2A, 2B, 2C, and 2D. FIG. 2A illustrates a case where radiation is emitted perpendicularly to an overlapping portion of the radiographic imaging apparatuses D1 and D2. FIG. 2B illustrates a case where radiation is emitted from a position higher than a position perpendicular to the overlapping portion of the radiographic imaging apparatuses D1 and D2. FIG. 2C illustrates a case where radiation is emitted from a position lower than a position perpendicular to the overlapping portion of the radiographic imaging apparatuses D1 and D2. FIG. 2D illustrates a case where radiation having a lower tube voltage than that illustrated in FIG. 2A is emitted to the overlapping portion of the radiographic imaging apparatuses D1 and D2. As illustrated in FIGS. 2A, 2B, 2C, and 2D, the radiation is incident at various angles with various intensity on the radiographic imaging apparatuses D1 and D2 depending on a position of the radiation source 105. As illustrated in FIG. 2B, radiation X1 transmitting through an effective pixel area end of the radiographic imaging apparatus D1 reaches a position, on the radiographic imaging apparatus D2, lower than the effective pixel area end of the radiographic imaging apparatus D1 when seen from the radiation source 105. As illustrated in FIGS. 2A, 2B, 2C, and 2D, the strength of the image signal changes based on the radiation intensity. Accordingly, density of a structure to appear in a radiographic image can change. Moreover, a position of the structure appearing in the radiographic image can change based on an incident angle of the radiation.

Moreover, radiation X2 transmitting through an end portion of the casing 6 of the radiographic imaging apparatus D1 is incident on the radiographic imaging apparatus D2, as with the radiation X1. Consequently, a structure of a portion outside the effective pixel area end of the radiographic imaging apparatus D1 appears in an area (a width $L_A$), of a radiographic image to be acquired by the radiographic imaging apparatus D2, between a reaching point of the radiation X1 and a reaching point of the radiation X2. As a result, information of the examinee M is damaged in such a radiographic image.

Figure 3:
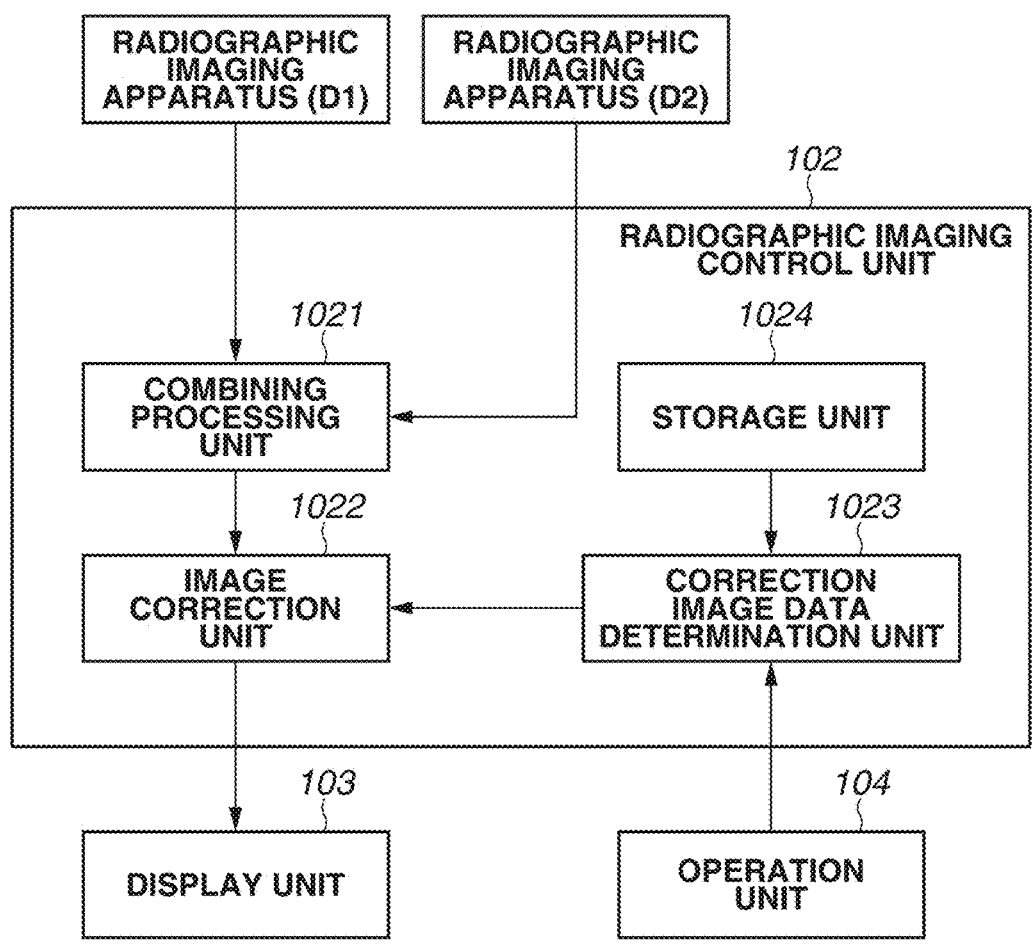
FIG. 3 is a block diagram illustrating a radiographic imaging control unit according to the first exemplary embodiment.

Next, the radiographic imaging control unit 102 according to the present exemplary embodiment is described with reference to FIG. 3. The radiographic imaging control unit 102 includes at least a combining processing unit 1021, an image correction unit 1022, and a correction image data determination unit 1023. The radiographic imaging control unit 102 further includes a storage unit 1024.

The combining processing unit 1021 combines a plurality of radiographic images to generate a stitched image. The plurality of radiographic images includes radiographic image data acquired by each of the radiographic imaging apparatuses D1 and D2. Among the radiographic images, a radiographic image acquired from the radiographic imaging apparatus D2 has an artifact in an area in which the radiographic imaging apparatuses D1 and D2 overlap. As for the area (a defect area) in which the radiographic imaging apparatuses D1 and D2 overlap, the combining processing unit 1021 uses a radiographic image acquired from the radiographic imaging apparatus D1 to generate a stitched image. This configuration can minimize an area of an artifact that occurs in the stitched image. Herein, the overlapping area includes an area in which a structure appears in a radiographic image.

The image correction unit 1022 performs correction processing on the stitched image output from the combining processing unit 1021 so that the artifact becomes indistinctive. In the present exemplary embodiment, the stitched image undergoes processing for subtracting correction image data serving as image data including structure information of the radiographic imaging apparatus. Herein, the structure information represents information indicating a radiographic imaging apparatus structure appearing in a radiographic image. The structure information includes a radiation attenuation coefficient, a thickness, and arrangement of a substance inside the radiographic imaging apparatus. The substance can include the radiation detection panel 2, the flexible circuit substrate 8, the printed circuit board 5, integrated circuits mounted on these units, or other components constituting these units.

The correction image data determination unit 1023 determines correction image data to be used by the image correction unit 1022 based on the imaging conditions of a radiographic image. Herein, since structure appearing position and density of the structure information in the correction image data differ according to the imaging conditions, correction image data with which a defect of the stitched image becomes indistinctive can be selected based on the imaging conditions. In the present exemplary embodiment, the correction image data can be selected and determined based on the correction image data stored in the storage unit 1024.

The storage unit 1024 stores a plurality of pieces of correction image data. Each of the plurality of pieces of correction image data is associated with a plurality of imaging conditions and stored in the storage unit 1024. In one example, a plurality of pieces of correction image data is associated with a plurality of imaging conditions according to a correction image data table. FIG. 4 illustrates one example of the correction image data table. Herein, the distance X, the height Y, and the depth Z illustrated in FIG. 1, a tube voltage value, and a correction image data are associated and stored as the imaging conditions. Such imaging conditions illustrated in FIG. 4 are merely one example, and are not limited thereto.

Subsequent to such processing, the radiographic imaging control unit 102 may display the corrected stitched image on the display unit 103.

Figure 5:
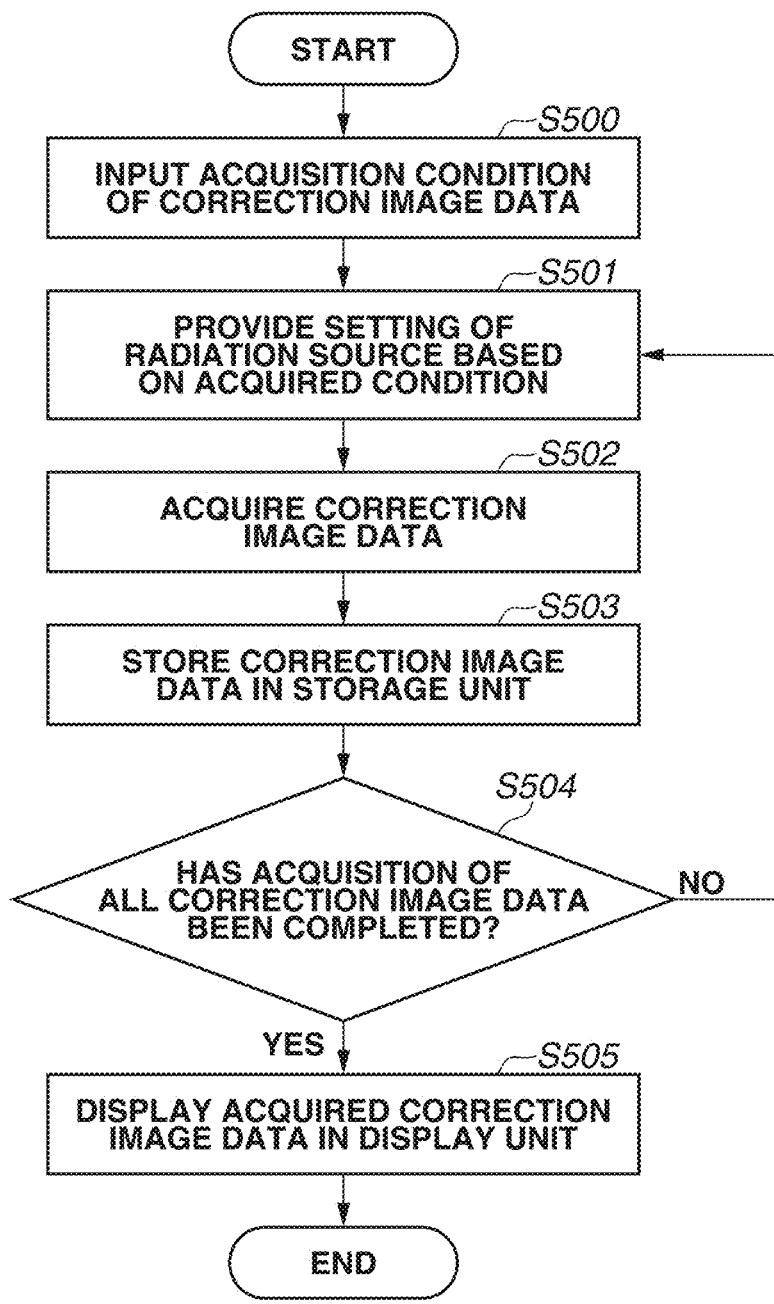
FIG. 5 is a flowchart illustrating processing performed when correction image data is acquired according to the first exemplary embodiment.

Next, acquisition processing of correction image data is described with reference to the flowchart of FIG. 5. The radiographic imaging control unit 102 controls the acquisition processing, and the correction image data is stored in the storage unit 1024.

In step S500, an operator inputs a correction image data acquisition condition to the radiographic imaging control unit 102. The operator uses, for example, the operation unit 104 to input the condition. For the acquisition conditions, conditions that can be set as the imaging conditions are input. For example, the operator can set conditions as many as the number of correction image data tables illustrated in FIG. 4. In step S501, the radiographic imaging control unit 102 performs a setting of the radiation source 105 via the radiation generation control unit 101 based on the acquisition condition. The radiographic imaging control unit 102 determines a position of the radiation source 105 based on the acquisition condition, and determines the setting.

In step S502, the radiographic imaging control unit 102 acquires correction image data. More specifically, the radiographic imaging control unit 102 causes the radiation source 105 to irradiate the radiographic imaging apparatuses D1 and D2 with radiation without an examinee, and acquires a radiographic image including structure information. In step S503, the radiographic imaging control unit 102 stores the radiographic image in the storage unit 1024 as correction image data. In step S504, the radiographic imaging control unit 102 checks whether correction image data for all the acquisition conditions has been acquired. If the radiographic imaging control unit 102 determines that the acquisition is completed (YES in step S504), the processing proceeds to step S505. On the other hand, if the radiographic imaging control unit 102 determines that the acquisition is not completed (NO in step S504), the processing returns to step S501. Then, the processing from step S501 to step S503 is repeated.

Figure 6:
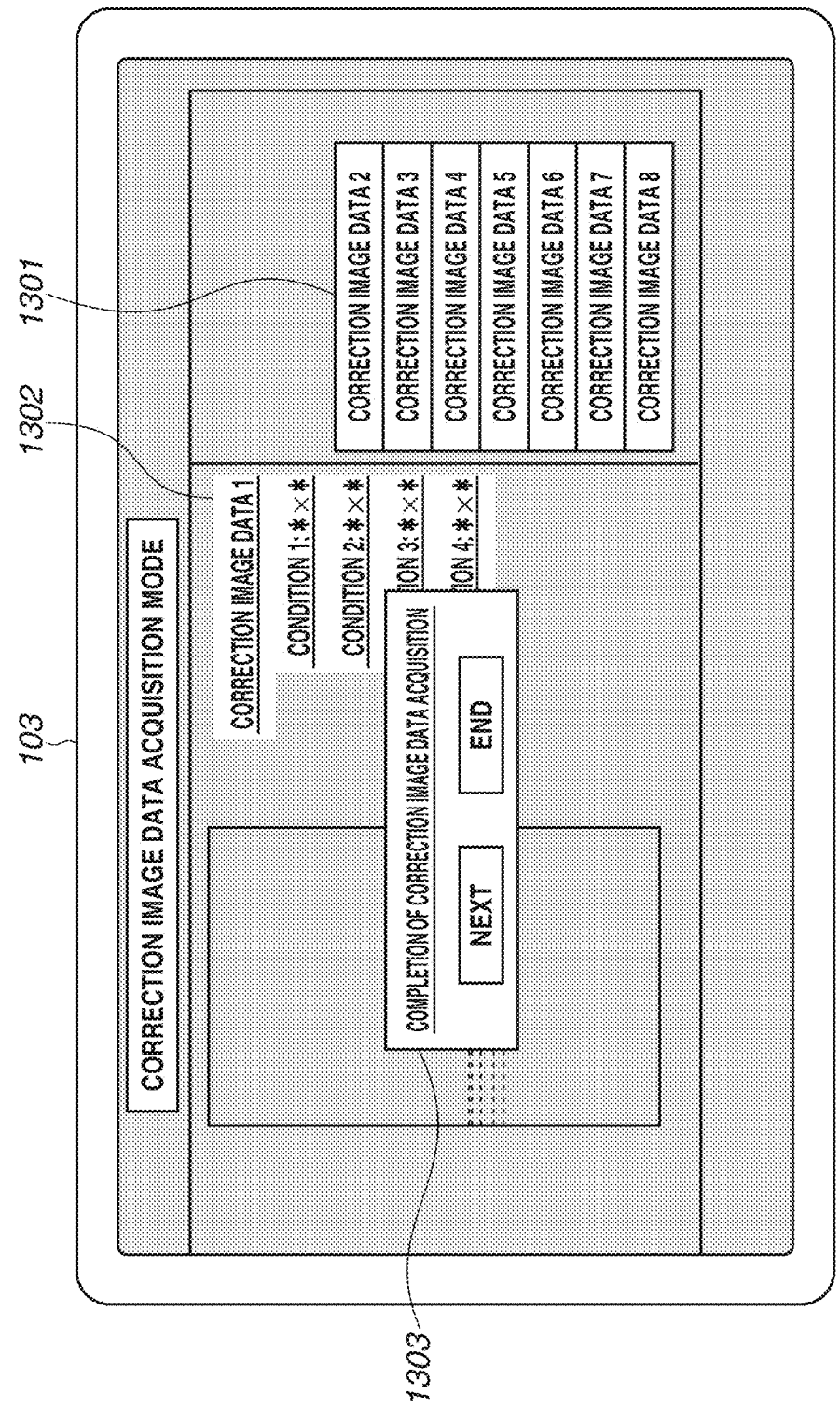
FIG. 6 is a diagram illustrating a display style of a display unit after the correction image data is acquired according to the first exemplary embodiment.

In step S505, the radiographic imaging control unit 102 displays the acquired correction image data on the display unit 103. FIG. 6 is a diagram illustrating a display style of the display unit 103 after the acquisition of the correction image data. As illustrated in FIG. 6, the display unit 103 can display a message 1303 that can be used to confirm whether to acquire correction image data, or whether to end acquisition of the correction image data. An area 1302 indicates correction image data that is currently displayed. An area 1301 indicates a correction image data group that has been acquired or is scheduled to be acquired. In this manner, the use of the display unit 103 can check the acquired correction image data. Moreover, such a method for acquiring correction image data is merely one example, and is not limited thereto.

Next, correction processing performed by the image correction unit 1022 of the radiographic imaging system 100 according to the present exemplary embodiment is described with reference to FIGS. 7A, 7B, and 7C. In particular, the correction processing reduces a defect area caused by appearance of structure information of the radiographic imaging apparatus D1 from the radiographic imaging apparatus D2.

FIG. 7A illustrates a stitched image 700 that is generated by combining a plurality of radiographic image data (radiographic images) by the combining processing unit 1021.

FIG. 7B illustrates one example of structure information to be used in the correction processing performed by the image correction unit 1022. Herein, the structure information includes correction image data 701 which is acquired under predetermined imaging conditions.

FIG. 7C illustrates a corrected stitched image 702 that is acquired by correcting a defect area, in which a structure appears, on the stitched image 700 as illustrated in FIG. 7A. The corrected stitched image 702 is an output of the image correction unit 1022. Moreover, an image 7001 illustrated in FIG. 7A represents a radiographic image output from the radiographic imaging apparatus D1. In the example illustrated in FIG. 7A, the image 7001 mainly includes the upper body of the examinee. An image 7002 illustrated in FIG. 7A represents a radiographic image output from the radiographic imaging apparatus D2. In the example illustrated in FIG. 7A, the image 7002 mainly includes the lower body of the examinee. The combining processing unit 1021 combines the radiographic images based on an arrangement relationship of radiation detection areas of the radiographic imaging apparatus D1 and D2 so that an area of the defect area on the stitched image is minimized. Moreover, the combining processing unit 1021 can acquire the corrected stitched image 702 by subtracting the correction image data 701 from the combined stitched image 700.

Next, a method for determining correction image data from a correction image data table stored in the storage unit 1024 is described with reference to FIG. 8. Among a plurality of pieces of correction image data stored in the storage unit, correction image data suitable for correction of the structure information is set. First, the correction image data determination unit 1023 compares imaging conditions with imaging conditions associated with a correction image data table. Herein, the correction image data determination unit 1023 selects a correction image data having the smallest difference between a setting value of each imaging condition in image capturing and the imaging conditions associated with the correction image data table.

More specifically, such a method is described with reference to FIG. 8. For example, assume that there is a correction data table illustrated in FIG. 8, and an image is captured under the following imaging conditions. Herein, the imaging conditions include a height of 113 cm, a distance of 168 cm, a depth of I, and a tube voltage of J. Herein, each of the depth I and the tube voltage J is an optional constant for the sake of simplicity of the description. First, the correction image data determination unit 1023 compares a height among the imaging conditions with correction image data, and recognizes that the height of 113 cm is a value between 110 cm and 115 cm. Next, the correction image data determination unit 1023 compares two pieces of data in the correction data table, and selects 115 cm, which is a correction table data value with smaller difference. The correction image data determination unit 1023 performs similar determination processing with respect to a distance, and selects 170 cm, accordingly.

The correction image data determination unit 1023 determines that "f" in the correction table data is to be used for correction.

In the present exemplary embodiment, as described above, the radiographic imaging system 100 includes the plurality of radiographic imaging apparatuses D1 and D2 each acquiring a radiographic image, and the combining processing unit 1021 configured to combine a plurality of radiographic images acquired by the plurality of radiographic imaging apparatuses D1 and D2 and to generate a stitched image. The radiographic imaging system 100 determines correction image data based on imaging conditions, and can correct the stitched image using the correction image data. As a result, the corrected stitched image can reduce structure information.

A second exemplary embodiment of the present invention is described with reference to FIG. 9. FIG. 9 illustrates a correction data table according to the present exemplary embodiment. First, a description is given of a difference between the first exemplary embodiment and the present exemplary embodiment. In the first exemplary embodiment, the correction image data determination unit 1023 selects correction image data to be used for correction of a stitched image from a plurality of pieces of correction image data stored in the storage unit 1024. By contrast, in the present exemplary embodiment, a correction image data determination unit 1023 generates correction image data to be used for correction of a stitched image from a plurality of pieces of correction image data stored in a storage unit 1024. More specifically, a plurality of pieces of correction image data is selected based on imaging conditions, and data to be interpolated is calculated from the plurality of pieces of selected correction image data. Then, correction image data suitable for the imaging conditions is determined. In the following description, the correction image data determination unit 1023 calculates height, distance, and tube voltage values for generation of correction image data. However, the present exemplary embodiment is not limited thereto. Moreover, components similar to those of the first exemplary embodiment will be given the same reference numerals as above, and description thereof will be omitted.

First, a calculation method for height and distance is described. The calculation processing is performed by the correction image data determination unit 1023 or a component of a radiographic imaging control unit 102. First, a setting value input from an operation unit 104 or a setting value of each imaging condition that is set beforehand and a correction data table value are compared. Subsequently, two conditions having small differences between imaging conditions and imaging conditions in the correction table are selected for each condition. First, assume that imaging conditions include a height of 113 cm, a distance of 168 cm, a depth of I, and a tube voltage of J. Herein, each of the depth I and the tube voltage J is an optional value. Among the imaging conditions, selection of the height is first described. The correction image data determination unit 1023 compares the height with the correction table data. Then the correction image data determination unit 1023 recognizes that the height is a value between 110 cm and 115 cm, and selects "110 cm" and "115 cm" from the correction table data. Subsequently, the correction image data determination unit 1023 calculates a value of correction table data that has a smaller difference when the imaging conditions and the correction table data are compared. From the calculation result, the correction image data determination unit 1023 selects "115 cm" as a height of correction table data that is the closest to the correction table. The correction image data determination unit 1023 calculates a distance. Similarly, the correction image data determination unit 1023 selects "170 cm" from the correction table data.

Next, the correction image data determination unit 1023 calculates a tube voltage change ratio based on a tube voltage value of the correction data table, the calculated height data, and the calculated distance data, to calculate a tube voltage. The correction image data determination unit 1023 calculates a combination including the above two sets of data from the correction data table. As a result, the correction image data determination unit 1023 selects "f" and "e" including height data, and "Y" and "f" including distance data. The correction image data determination unit 1023 calculates one piece of correction image data from these three pieces of correction image data. For example, the correction image data determination unit 1023 can generate one piece of correction image data by performing addition averaging on the three pieces of correction image data. Similarly, one piece of correction image data can be generated by performing addition averaging on tube voltage values and height values.

Moreover, a value J of the tube voltage can be changed. From the correction image data, the correction image data determination unit 1023 selects j as a value that is the closest to the value of a tube voltage N in the imaging conditions and is smaller than the value of the tube voltage N. Moreover, from the correction image data, the correction image data determination unit 1023 selects J as a value that is the closest to the tube voltage N in the imaging conditions and is greater than the value of the tube voltage N. Subsequently, from the correction table data including the tube voltage j and the tube voltage J, the correction image data determination unit 1023 selects a value having a small difference in height and distance in the imaging conditions with respect to a position of height and distance of correction table data for the voltage value j. The use of the plurality of pieces of selected correction image data enables the correction image data determination unit 1023 to generate correction image data in consideration of a tube voltage value.

In the present exemplary embodiment, as described above, the radiographic imaging system 100 generates new correction image data from a plurality of pieces of correction image data, and uses the generated correction image data for correction of a stitched image. Accordingly, structure information can be reduced more effectively than the first exemplary embodiment.

A third exemplary embodiment of the present invention is described with reference to FIGS. 10A and 10B each illustrating a position display unit 800 provided in a radiation source according to the present exemplary embodiment. First, a description is given of a difference between the first exemplary embodiment and the present exemplary embodiment. In the present exemplary embodiment, a radiographic imaging control unit 102 transmits imaging conditions corresponding to correction image data to a radiation generation control unit 101, which is different from the first exemplary embodiment. In the present exemplary embodiment, the radiographic imaging control unit 102 has a function as a transmission unit for transmitting the imaging conditions corresponding to the correction image data to the radiation generation control unit 101. Moreover, the imaging conditions corresponding to the correction image data includes position information about positions of a plurality of radiographic imaging apparatuses and the radiation source when the correction image data is acquired.

First, the radiographic imaging control unit 102 transmits the imaging conditions corresponding to the correction image data to the radiation generation control unit 101. Herein, the radiographic imaging control unit 102 (a correction image data determination unit 1023) selects correction image data to be used in the next imaging based on an input from an operation unit 104, correction image data stored in a storage unit 1024, and an input from the radiation generation control unit 101. For example, the transmission unit transmits position information including a height of 115 cm, a distance of 170 cm and a depth of 0 cm as imaging conditions corresponding to the correction image data to the radiation generation control unit 101.

Further, the radiation generation control unit 101 has a function of transmitting the position information received from the radiographic imaging control unit 102 to the radiation source 105. The radiation generation control unit 101 further has a function of receiving the position information from the radiation source 105. In addition, the radiation generation control unit 101 can perform control so that a radiation irradiation permission signal is not output until the position information transmitted to the radiation source 105 matches actual position information received from the radiation source 105.

FIGS. 10A and 10B illustrate the radiation source 105 of the present exemplary embodiment. The radiation source 105 includes the position display unit 800 with a display that is changed based on a difference between the position information about positions of a plurality of radiographic imaging apparatuses and the position information transmitted from the transmission unit through the radiation generation control unit 101. One example of the position display unit 800 includes five visual indicators (lamps). FIG. 10A illustrates an example case in which a right-direction lamp 801 is turned on. The example case illustrated in FIG. 10A indicates that a difference between two pieces of position information is present in a depth direction. If there is a difference between the position information corresponding to the correction image data and the position of the radiation source 105, the radiation generation control unit 101 lights a lamp to guide the radiation source 105. The radiation generation control unit 101 causes the position display unit 800 to turn the light on to guide the radiation source 105 toward a direction which is indicated by a lamp of the position display unit 800 being turned on, so that the radiation source 105 can be moved to a correctable position where a correction of a stitched image can be made using the correction image data. In the position display unit 800, a center lamp 802 indicates a back-and-forth movement instruction. When the light of the center lamp is constantly on, it indicates a forth movement. When the center lamp blinks, it indicates a back movement. If the position information corresponding to the correction image data matches the position information of the radiation source 105, the radiation generation control unit 101 controls the position display unit 800 so that all the lamps are turns off.

When the operator moves the radiation source 105 to the correctable position, a stitched image can be corrected with more accuracy. In such a case, the position of the radiation source 105 is manually adjusted by the operator.

As described above, with the use of the correction image data, a stitched image can be suitably generated under correctable imaging conditions.

A fourth exemplary embodiment of the present invention is described. In the present exemplary embodiment, similar to the third exemplary embodiment, a radiographic imaging control unit 102 transmits imaging conditions corresponding to correction image data to a radiation generation control unit 101. The radiation generation control unit 101 according to the present exemplary embodiment can automatically control a position of a radiation source 105 based on a difference between the imaging conditions (position information) corresponding to the correction image data and position information of the radiation source 105 so that the difference is reduced. Accordingly, with the use of correction image data, a stitched image can be suitably generated under a correctable imaging condition.

Moreover, in a radiographic imaging system 100 according to the present exemplary embodiment, the radiation source 105 automatically moves based on acquisition conditions of correction image data. This configuration automates the positioning of the position information in step S501 of the flowchart illustrated in FIG. 5. Hence, a correction image data table can be readily acquired.

A fifth exemplary embodiment of the present invention is described with reference to FIGS. 11A and 11B. Unlike the other exemplary embodiments, a radiographic imaging control unit 102 according to the present exemplary embodiment transmits a signal for control of a radiation source 105 to a radiation generation control unit 101 so that radiation is not emitted. The radiation generation control unit 101 controls the radiation source 105 based on the received signal so that the radiation is not emitted. In the present exemplary embodiment, the radiographic imaging control unit 102 functions as a transmission unit.

A radiographic imaging system 100 according to the fifth exemplary embodiment is described. For example, in a case where a position of the radiation source 105 is excessively higher or lower than an overlapping portion of radiographic imaging apparatuses D1 and D2, or a distance between the radiation source 105 and the overlapping portion of the radiographic imaging apparatuses D1 and D2 is short, information of an examinee may be lost from a radiographic image. In such a case, a stitched image may not be appropriately corrected even by the image correction unit described in the first exemplary embodiment. In other words, the radiation source 105 is arranged at a position where a correction of a stitched image cannot be made based on the correction image data.

Figure 11A:
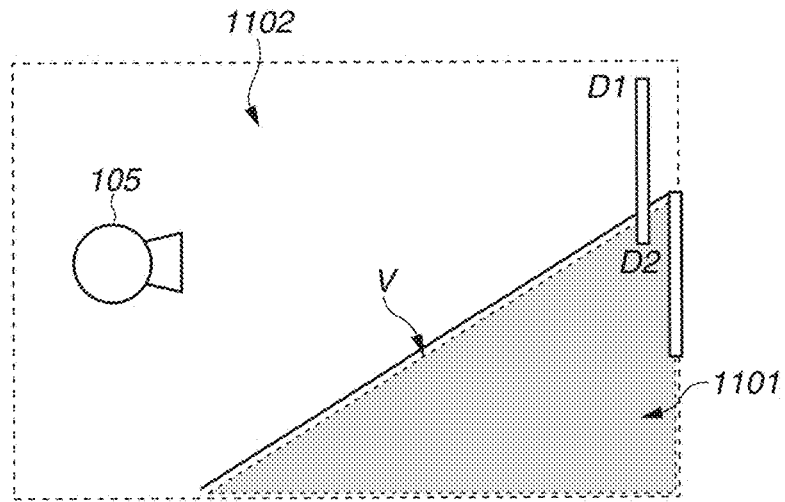
FIGS. 11A and 11B are diagrams illustrating arrangement of a plurality of radiographic imaging apparatuses according to a fifth exemplary embodiment of the present invention.
Figure 11B:
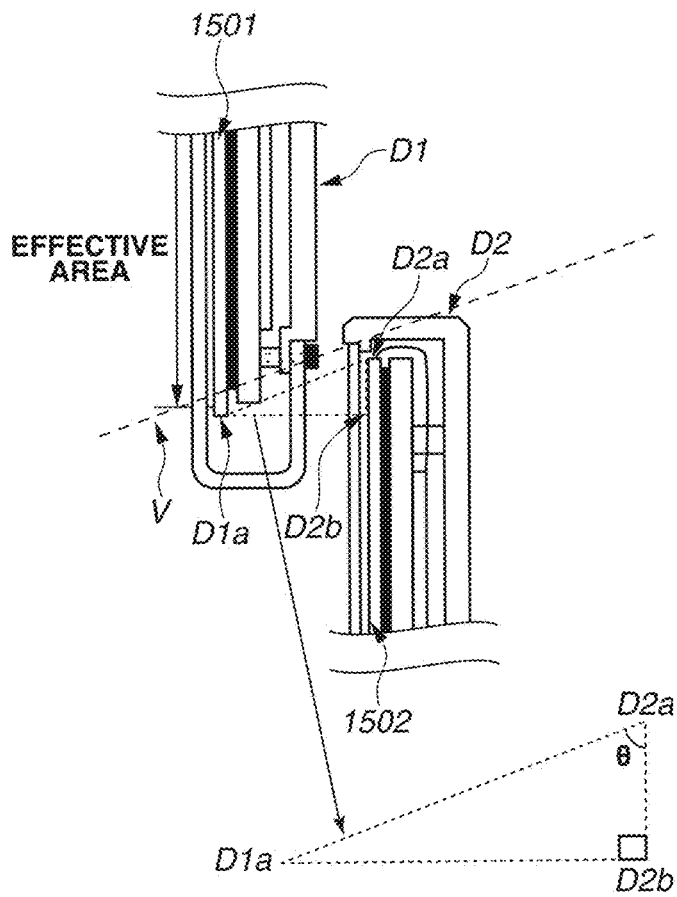

FIGS. 11A and 11B illustrate an example of arrangement of the radiation source 105 and the radiographic imaging apparatuses D1 and D2 according to the present exemplary embodiment. In FIGS. 11A and 11B, a boundary line V indicates a boundary whether the radiographic imaging system 100 can capture an image. In a case where the radiation source 105 is arranged at a position substantially equal to or lower than that of the boundary line V, the radiation generation control unit 101 prohibits emission of radiation. In other words, an area 1101 is a range in which emission of radiation by the radiation source 105 is restricted. The boundary line V is defined, for example, based on whether a radiographic image can be acquired by each of the radiographic imaging apparatuses D1 and D2. Moreover, the boundary line V can be defined based on whether the correction can be made in a range based on correction image data. If the radiation source 105 is arranged above the boundary line V, the radiation generation control unit 101 permits emission of radiation from the radiation source 105. In other words, an area 1102 is a range in which emission of radiation by the radiation source 105 is permitted. Herein, a description is given of determination of a radiation irradiation restricted range defined by the boundary line V. The radiographic imaging apparatuses D1 and D2 illustrated in FIG. 11A respectively include radiation detection surfaces 1501 and 1502 as illustrated in FIG. 11B. Herein, the radiation detection surfaces 1501 and 1502 respectively have detection ends D1a and D2a as end portions. A line that extends from the detection end D1a and is perpendicular to the radiation detection surface 1502 contacts the radiation detection surface 1502 at a contact point D2b. A triangle formed by the detection end D1a, the detection end D2a, and the contact point D2b has an angle θ that is determined as follows.

$$\text{Angle } \theta = \text{atan}\left(\frac{\text{distance from } D1a \text{ to } D2b}{\text{distance from } D2a \text{ to } D2b}\right) \quad \text{[Expression 1]}$$

The radiographic imaging system 100 according to the present exemplary embodiment restricts an area in which emission of radiation by the radiation source 105 is permitted to be inside the boundary line V. This configuration prevents missing information of an examinee. Moreover, radiographic images for a stitched image can be captured within a correctable range.

A sixth exemplary embodiment of the present invention is described with reference to FIGS. 12A and 12B. Unlike the fifth exemplary embodiment, three radiographic imaging apparatuses D1, D2, and D3 are arranged according to the present exemplary embodiment. FIGS. 12A and 12B illustrate the radiographic imaging apparatuses D1, D2, and D3 and a radiation source 105 according to the present exemplary embodiment. Components similar to those of the fifth exemplary embodiment are not illustrated in the drawings, and the description thereof is omitted. The middle radiographic imaging apparatus D2 in FIG. 12A is arranged in the rear of the radiographic imaging apparatuses D1 and D3. In FIG. 12B, on the other hand, the middle radiographic imaging apparatus D2 is arranged in front of the radiographic imaging apparatuses D1 and D3.

In FIGS. 12A and 12B, an area 1202 defined by boundary lines V and V' serves as an area in which emission of radiation from the radiation source 105 is permitted by a radiation generation control unit 101. Moreover, an area 1201 serves as an area in which the radiation generation control unit 101 prohibits emission of radiation from the radiation source 105. The method for defining a boundary line is similar to that of the fifth exemplary embodiment.

As illustrated in FIGS. 12A and 12B, an area in which the radiation source 105 is permitted to emit radiation differs depending on arrangement of the radiographic imaging apparatuses.

If a distance between an intersection point K of the boundary lines V and V' and the center of the radiographic imaging apparatus D2 is zero, such a state indicates that the radiographic imaging apparatuses D1, D2, and D3 are aligned in a height direction without an overlapping area.

In the present exemplary embodiment, as illustrated in FIG. 12B, the middle radiographic imaging apparatus D2 is positioned near the radiation source 105, and the intersection point K is set near the radiographic imaging apparatus D2, so that a setting range of the radiation source 105 is determined.

The radiographic imaging system 100 can include a notification unit for notifying that the radiation source 105 is moved outside the area 1201. The notification unit may ring an alarm, or include an alarm lamp or a monitor to display a state of the radiation source 105. Alternatively, the radiographic imaging system 100 may perform a control operation so that the radiation generation control unit 101, a radiographic imaging control unit 102, or a display unit 103 displays a state of the radiation source 105.

Each of the exemplary embodiments of the present invention can be also carried out by a computer or a control computer that executes a program (a computer program). Moreover, a unit such as a computer-readable recording medium or a transmission medium for supplying a program to a computer can be applied as each exemplary embodiment of the present invention. For example, the recording medium includes a compact disc-read-only memory (CD-ROM) in which the program is stored, and the transmission medium such as Internet transmits the program. Moreover, such a program can be applied as each exemplary embodiment of the present invention. The program, the recording medium, the transmission medium, and a program product are encompassed by the scope of the present invention. Moreover, an invention which can be readily conceived by a combination of the exemplary embodiments are encompassed within the scope of the present invention.

While the present invention has been described with reference to the exemplary embodiments, it is to be understood that the invention is not limited to the exemplary embodiments, and various modifications can be made without departing from the scope of the disclosure. Further, a part of the above-described exemplary embodiments may be combined with each other as needed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-072863, filed Mar. 31, 2015, which is hereby incorporated by reference herein in its entirety.

What is claimed is:

1. A radiographic imaging system including a plurality of radiographic imaging apparatuses each configured to acquire a radiographic image based on radiation emitted from a radiation source and a processing unit configured to combine a plurality of the radiographic images acquired from the plurality of radiographic imaging apparatuses to generate a stitched image, the radiographic imaging system comprising:
    a correction image data determination unit configured to determine correction image data based on an irradiation condition of radiation emitted from the radiation source; and
    an image correction unit configured to correct an area of the stitched image corresponding to an area in which the plurality of radiographic imaging apparatuses overlap each other, by using the correction image data.

2. The radiographic imaging system according to claim 1, wherein the irradiation condition includes position information about positions of the plurality of radiographic imaging apparatuses and the radiation source.

3. The radiographic imaging system according to claim 2, wherein the position information includes an incident angle between each of the radiographic imaging apparatuses and radiation emitted from the radiation source.

4. The radiographic imaging system according to claim 1, wherein the irradiation condition includes a value relating to a tube voltage of the radiation source.

5. The radiographic imaging system according to claim 1, wherein the correction image data includes image data including structure information of the radiographic imaging apparatus.

6. The radiographic imaging system according to claim 5, wherein the structure information includes information about a casing of the radiographic imaging apparatus or at least one of thickness and arrangement of a part housed in the casing.

7. The radiographic imaging system according to claim 1, further comprising a storage unit configured to store a plurality of pieces of the correction image data,
    wherein, the correction image data determination unit determines correction image data to be used for correction of the stitched image based on the plurality of pieces of correction image data stored in the storage unit.

8. The radiographic imaging system according to claim 7, wherein the correction image data determination unit selects correction image data to be used for correction of the stitched image from the plurality of pieces of correction image data stored in the storage unit.

9. The radiographic imaging system according to claim 7, wherein the correction image data determination unit generates correction image data to be used for correction of the stitched image from the plurality of pieces of correction image data stored in the storage unit.

10. The radiographic imaging system according to claim 1, further comprising a transmission unit configured to transmit an irradiation condition corresponding to the correction image data to a radiation generation control unit controlling the radiation source.

11. The radiographic imaging system according to claim 10,
    wherein the irradiation condition corresponding to the correction image data includes position information about positions of the plurality of radiographic imaging apparatuses and the radiation source at time of acquisition of the correction image data, and
    wherein the radiation generation control unit includes a position display unit in which a display is changed based on a difference between the position information about the positions of the plurality of radiographic imaging apparatuses and the radiation source and position information transmitted from the transmission unit.

12. The radiographic imaging system according to claim 11, wherein the radiation generation control unit controls a position of the radiation source so that the difference is reduced.

13. The radiographic imaging system according to claim 11, wherein, in a case where the radiation source is arranged at a position at which a correction of the stitched image cannot be made based on the correction image data, the transmission unit transmits a signal for control of the radiation source to the radiation generation control unit so that radiation is not emitted.

14. The radiographic imaging system according to claim 1, wherein each of the radiographic imaging apparatuses includes a radiation detection panel configured to convert the emitted radiation into an image signal.

15. A control method for a radiographic imaging system including a plurality of radiographic imaging apparatuses each configured to acquire a radiographic image and a processing unit configured to combine a plurality of the radiographic images acquired from the plurality of radiographic imaging apparatuses to generate a stitched image, the control method comprising:
    determining correction image data based on an irradiation condition of radiation emitted from a radiation source; and
    correcting an area of the stitched image corresponding to an area in which the plurality of radiographic imaging apparatuses overlap, by using the correction image data.

16. A non-transitory computer-readable storage medium storing a program for causing a computer to perform a control method for a radiographic imaging system including a plurality of radiographic imaging apparatuses each configured to acquire a radiographic image and a processing unit configured to combine a plurality of the radiographic images acquired from the plurality of radiographic imaging apparatuses to generate a stitched image, the control method comprising:
    determining correction image data based on an irradiation condition of radiation emitted from a radiation source; and
    correcting an area of the stitched image corresponding to an area in which the plurality of radiographic imaging apparatuses overlap, by using the correction image data.

* * * * *